(12) United States Patent
Trapp et al.

(10) Patent No.: US 9,622,770 B2
(45) Date of Patent: Apr. 18, 2017

(54) CEREBRAL VASCULATURE DEVICE

(71) Applicant: W. L. Gore & Associates, Inc., Newark, DE (US)

(72) Inventors: Benjamin M. Trapp, Flagstaff, AZ (US); Nathan L. Friedman, Flagstaff, AZ (US); Michael J. Vonesh, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/535,253

(22) Filed: Nov. 6, 2014

(65) Prior Publication Data

US 2015/0127035 A1 May 7, 2015

Related U.S. Application Data

(63) Continuation of application No. 11/526,269, filed on Sep. 22, 2006, now abandoned.

(51) Int. Cl.
*A61M 29/00* (2006.01)
*A61B 17/3207* (2006.01)
(Continued)

(52) U.S. Cl.
CPC .. *A61B 17/320725* (2013.01); *A61B 17/1214* (2013.01); *A61B 17/12022* (2013.01); *A61B 17/12045* (2013.01); *A61B 17/12109* (2013.01); *A61B 17/12113* (2013.01); *A61B 17/12172* (2013.01); *A61F 2/013* (2013.01); *A61B 17/221* (2013.01); *A61B 2017/12127* (2013.01); *A61B 2017/320716* (2013.01); *A61F 2002/016* (2013.01); *A61F 2002/018* (2013.01); *A61F 2230/0065* (2013.01);
(Continued)

(58) Field of Classification Search
CPC .. A61B 17/320725; A61B 2017/12127; A61B 17/221; A61B 17/12109; A61B 17/12113; A61B 17/1214; A61B 17/12172; A61B 17/12022; A61B 17/12045; A61B 2017/320716; A61F 2230/0071; A61F 2230/0078; A61F 2002/016; A61F 2002/018; A61F 2/013; A61F 2230/0065; A61F 2230/0069

See application file for complete search history.

(56) References Cited

U.S. PATENT DOCUMENTS

| 3,435,826 A | 4/1969 | Fogarty |
| 3,467,101 A | 9/1969 | Fogarty et al. |

(Continued)

FOREIGN PATENT DOCUMENTS

| JP | 2001-509413 | 7/2001 |
| JP | 2005-000518 | 1/2005 |

(Continued)

*Primary Examiner* — Richard Louis

(57) ABSTRACT

Novel cerebral vasculature devices are disclosed, including thrombectomy removal devices that include a continuous braided structure, a proximal portion, a distal portion, and a first expandable portion located between the proximal portion and the distal portion. The braided structure includes a plurality of wires. The proximal portion and the distal portion include polymer imbedded at least partially into the braided structure. The device is useful for removing thrombus from a patient's vasculature.

17 Claims, 15 Drawing Sheets

(51) Int. Cl.
*A61B 17/12* (2006.01)
*A61F 2/01* (2006.01)
*A61B 17/221* (2006.01)

(52) U.S. Cl.
CPC ............... *A61F 2230/0069* (2013.01); *A61F 2230/0071* (2013.01); *A61F 2230/0078* (2013.01)

(56) References Cited

U.S. PATENT DOCUMENTS

| | | | |
|---|---|---|---|
| 3,996,938 A | 12/1976 | Clark, III | |
| 4,403,612 A | 9/1983 | Fogarty | |
| 5,496,330 A | 3/1996 | Bates et al. | |
| 5,575,818 A | 11/1996 | Pinchuk | |
| 5,800,525 A | 9/1998 | Bachinski et al. | |
| 5,895,398 A | 4/1999 | Wensel et al. | |
| 6,066,149 A | 5/2000 | Samson et al. | |
| 6,066,158 A | 5/2000 | Engelson et al. | |
| 6,096,053 A | 8/2000 | Bates | |
| 6,117,142 A | 9/2000 | Goodson et al. | |
| 6,123,715 A | 9/2000 | Amplatz | |
| 6,267,775 B1 | 7/2001 | Clerc et al. | |
| 6,638,257 B2 | 10/2003 | Amplatz | |
| 6,800,080 B1 | 10/2004 | Bates | |
| 6,929,634 B2 | 8/2005 | Dorros et al. | |
| 7,001,409 B2 | 2/2006 | Amplatz | |
| 2002/0038132 A1 | 3/2002 | Abrams | |
| 2003/0060833 A1* | 3/2003 | Carrison | A61B 17/221 606/108 |
| 2004/0024416 A1 | 2/2004 | Yodfat et al. | |
| 2004/0153118 A1 | 8/2004 | Clubb et al. | |
| 2004/0236369 A1 | 11/2004 | Dubrul | |
| 2005/0033311 A1 | 2/2005 | Guldfeldt et al. | |
| 2005/0049577 A1* | 3/2005 | Snell | A61M 25/0009 604/544 |
| 2006/0004440 A1 | 1/2006 | Stinson | |
| 2006/0036311 A1 | 2/2006 | Nakayama et al. | |
| 2006/0241690 A1 | 10/2006 | Amplatz et al. | |
| 2006/0247680 A1 | 11/2006 | Amplatz et al. | |
| 2007/0149996 A1 | 6/2007 | Coughlin | |

FOREIGN PATENT DOCUMENTS

| | | |
|---|---|---|
| WO | WO-9309915 A1 | 5/1993 |
| WO | 99/02093 | 1/1999 |
| WO | WO-03026487 A2 | 4/2003 |
| WO | WO-2004112879 A1 | 12/2004 |

\* cited by examiner

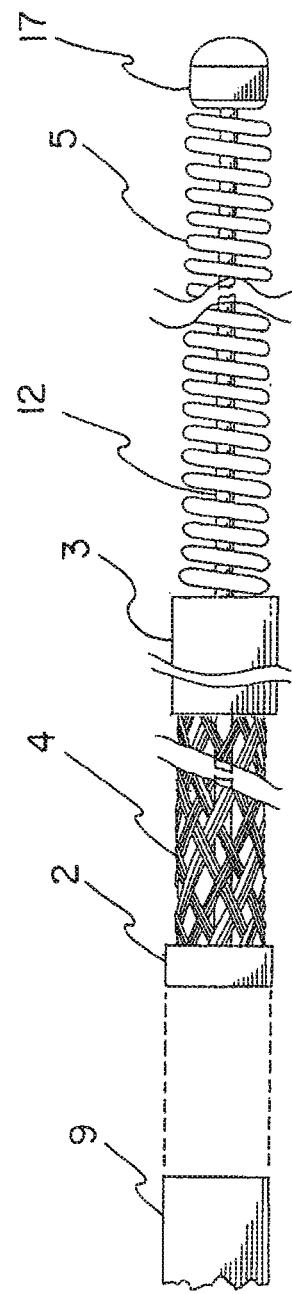
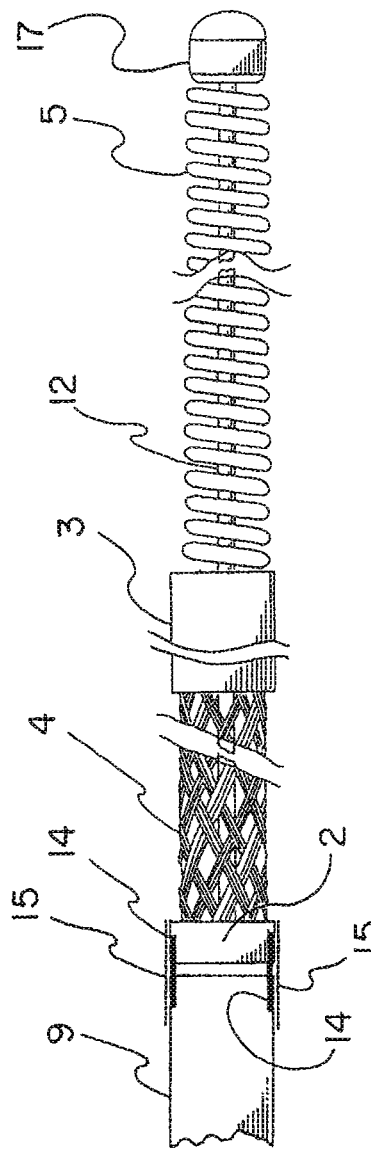
FIG. 4A
FIG. 4B

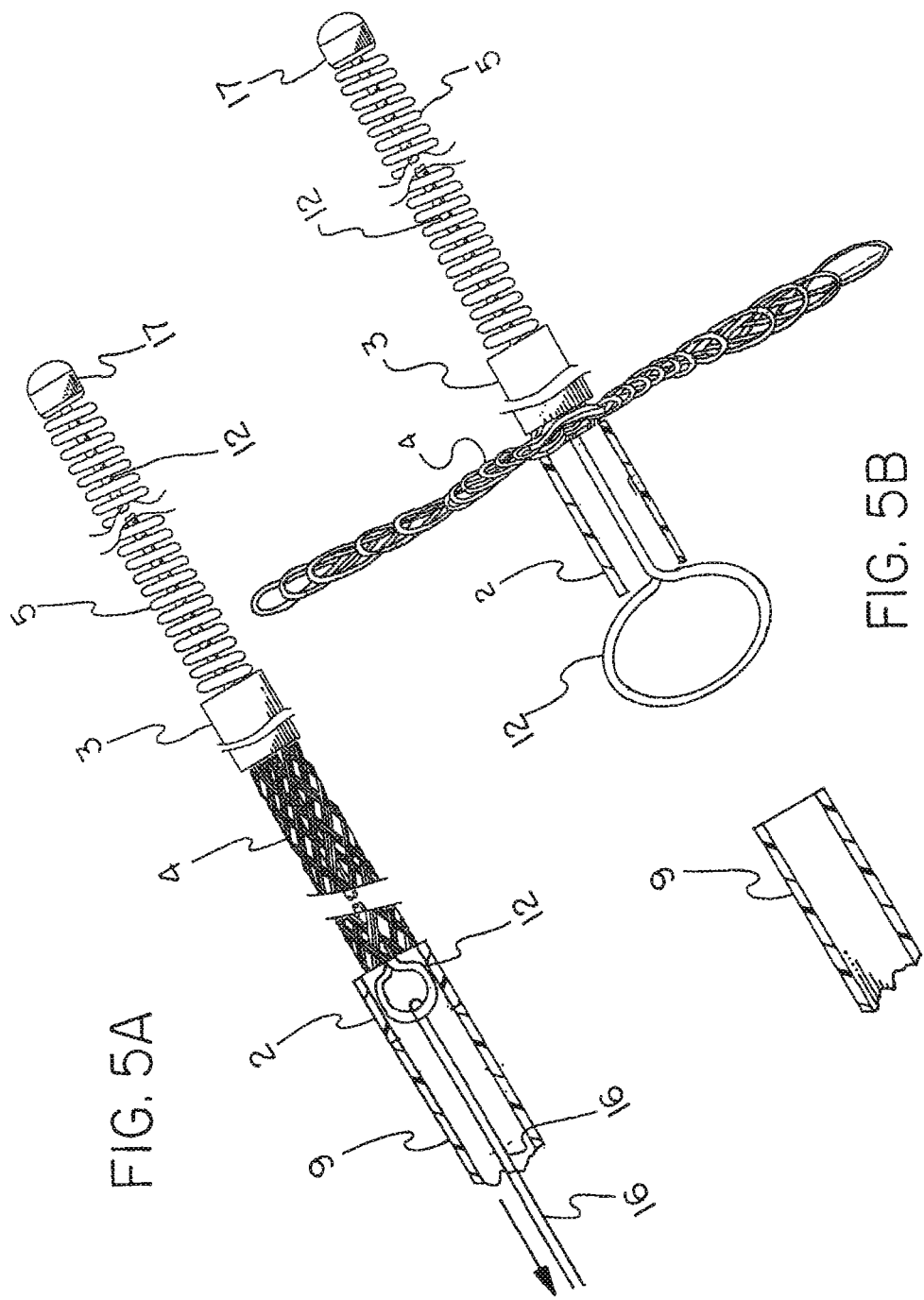

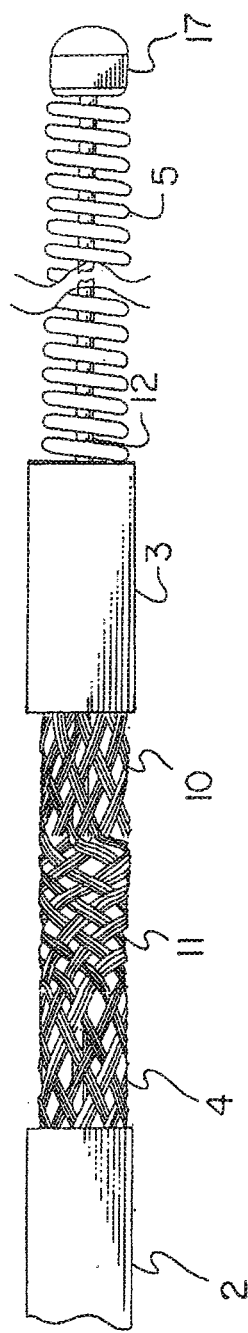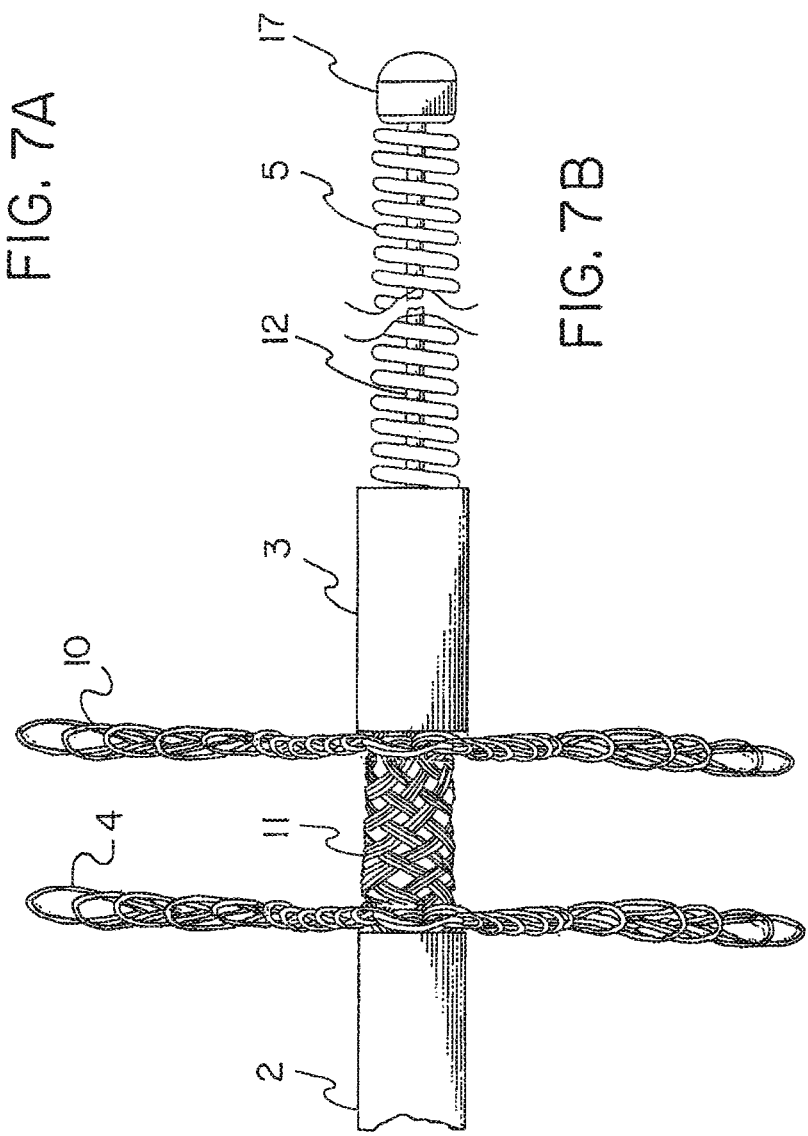
FIG. 7A
FIG. 7B

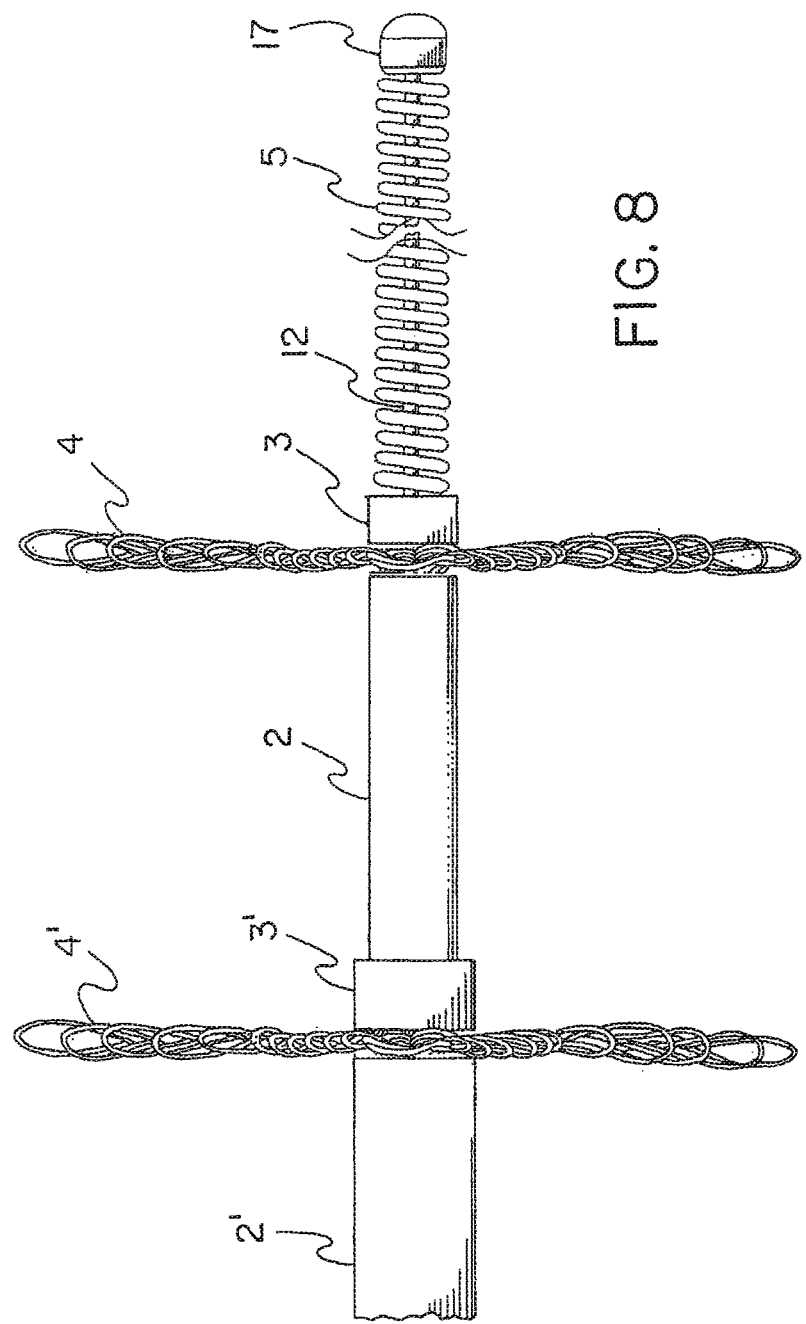

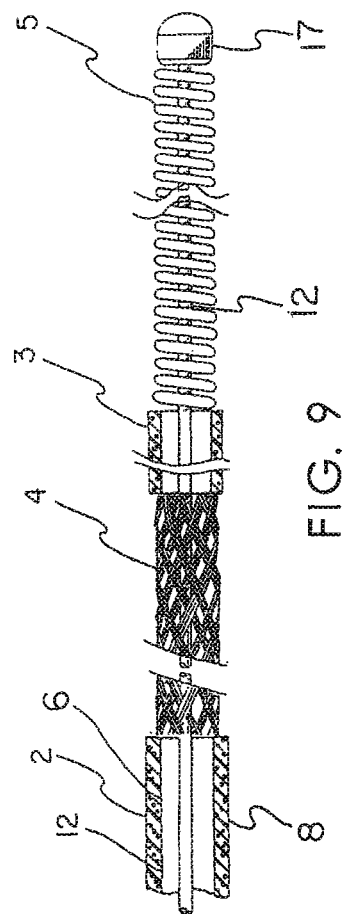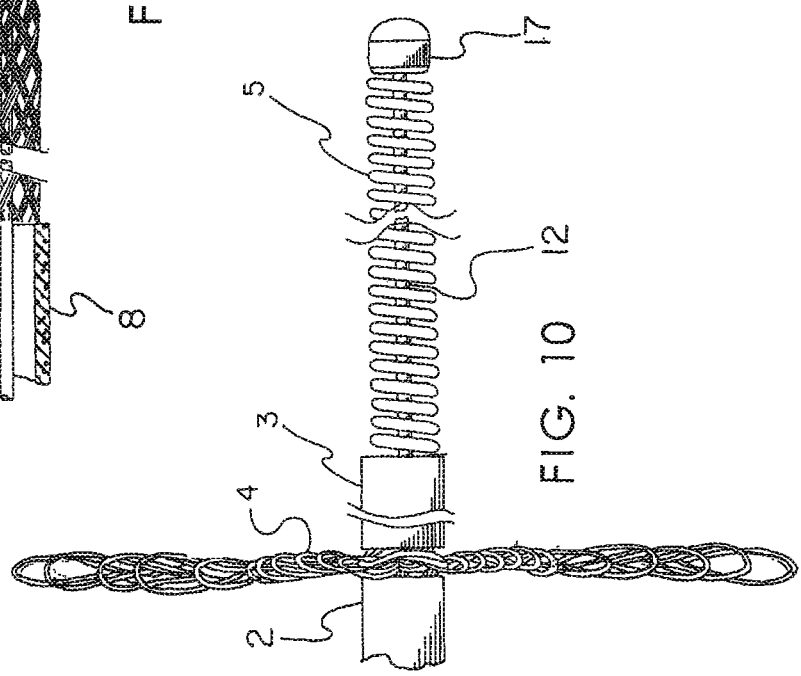

CEREBRAL VASCULATURE DEVICE

BACKGROUND OF THE INVENTION

1. Field of the Invention

The present invention relates to devices useful for removing objects such as thrombus/or other foreign bodies from a patient's vasculature. More particularly, the invention relates to devices useful for removing thrombus from a patient's cerebral vasculature.

2. Description of Related Art

The use of a mechanical means to restore patency to obstructed vessels is well known. These devices fit into many categories ranging from hydraulic removal of thrombus, rotating cutting blades for calcified plaque, inflatable means for crushing or dragging thrombus, or a multiplicity of metal structures that either self-expand or can be expanded to dredge a vessel or remove a stone.

Examples of these devices date back to the 'Fogarty Catheter' described by Fogarty in U.S. Pat. Nos. 3,367,101; 3,435,826; and 4,403,612 describing in detail improvements to a balloon catheter for embolectomy purposes. While suitable for many applications, dragging a balloon through the delicate, tortuous cerebral vasculature is not recommended. Crossing profiles of current state of the art balloon catheters would also limit their use with typical neurovascular accessories (e.g., microcatheters).

Mechanically expanded devices are also well known in the area of obstruction removal. Clark specifically focused on the use of an expanding braid for thrombus removal in U.S. Pat. No. 3,996,938. His teaching utilized a braid that would expand under the force of compression delivered by an inner core wire affixed to the distal end of the braid.

Many refinements on this theme have occurred in the areas of stone removal, clot removal, foreign body removal, etc. All of these are assemblies of some nature which either self-expand or mechanically expand under some delivered compressive load. Examples of these can be seen in Bates U.S. Pat. No. 6,800,080 in which parallel legs of the basket allow bodies to enter the retrieval basket; Bates U.S. Pat. No. 5,496,330 in which the basket is self-expanding and meant to collapse into a provided sheath; Engelson U.S. Pat. No. 6,066,158 describing a self-expanding conical basket held collapsed in a 'delivered' state because of a 'fixedly attached core wire'; and Samson U.S. Pat. No. 6,066,149 describing an assembly consisting of a series of braided expanders.

These devices, while elegant, fail to address the major concern for applications into the neurovasculature; namely, minimizing the crossing profile (i.e., the cross-sectional area) of the devices. In general, these are all assembled devices consisting of many components that need to either be welded in place, or fixedly attached using collars, etc. It is not seen how a device of these inventions would be compatible with physician preferred microcatheters used to access the delicate, tortuous neurovasculature.

In many of the inventions, the issue of crossing profile has been circumvented by describing fixed wire assemblies which are not meant to pass through a microcatheter, rather, they are meant to navigate from a large guiding catheter situated well proximal of the obstruction in large vasculature. Samson U.S. Pat. No. 6,066,149 is an example of this type of assembly. As demonstrated in the figures, the device is an assembly in which the wire ends are managed into a collar. The retractable core wire doubles as a conventional guidewire tip at its distal termination. This tip affords the steering of a guidewire and the ability to puncture a clot to cross it, while the large body of the device encompasses the expander. Perhaps suitable for easily accessible obstructions, this does not address the majority of anticipated cerebral vascular cases, or the physician preference, where a microcatheter/guidewire combination is used to create a pathway across the clot for angiographic visualization distal to the clot prior to the procedure.

Wensel has anticipated the need for smaller devices to achieve neurovasculature compatibility in U.S. Pat. No. 5,895,398. In this publication, he teaches the use of a helically shaped wire held straight for delivery by the microcatheter. By using a single wire shaped into a 'cork-screw' he has circumvented the complex assembly steps required in much of the other prior art resulting in large profiles. His invention, unfortunately, places the need of restraint on the microcatheter. Typically, physician preferred microcatheters are extremely flexible at the distal end lending little ability to hold a shaped wire straight. This results in a trade-off of making the 'cork-screw' floppy (which degrades its ability to extract a clot), or making a custom microcatheter which is stiff, limiting procedural access. Wensel's teaching also results in a structure which is not optimized for preventing the distal migration of particulate during the removal of clot due to the inherently large intertices of a device comprised of only a single, helically shaped wire.

SUMMARY OF THE INVENTION

The invention relates to cerebral vasculature devices and methods of making the same. The cerebral vasculature device comprises:

Continuous braided structure comprising a plurality of wires, the braided structure having a proximal portion, a distal portion, a first expandable portion between the proximal portion and the distal portion, and a lumen extending from the proximal portion to the distal portion;

The proximal portion and the distal portion each having an outer diameter and an inner diameter and further including polymer imbedded at least partially into the braided structure;

Core wire having a proximal end and a distal end, the core wire located within the lumen and extending from the braided structure proximal portion to a point at or distal to the braided structure distal portion; and Atraumatic component attached to the core wire distal end and having an outer diameter at least equal to the inner diameter of the braided structure distal portion.

DESCRIPTION OF THE DRAWINGS

The operation of the present invention should become apparent from the following description when considered in conjunction with the accompanying drawings, in which:

FIG. 4A shows the device of FIG. 3 and a catheter shaft according to an aspect of the invention;

FIG. 4B shows the device of FIG. 4A in its assembled form;

FIG. 5A shows in partial cross-section a further representative device according to an aspect of the invention;

FIG. 5B shows in partial cross-section the device of FIG. 5A with the expandable portion in its expanded state;

FIGS. 7A and 7B show a further embodiment according to an aspect of the invention;

FIG. 8 shows a further embodiment according to an aspect of the invention;

FIG. 9 is a longitudinal partial cross-section of a device according to an aspect of the invention;

FIG. 10 shows a device according to an aspect of the invention wherein a first expandable portion is in its expanded state;

DETAILED DESCRIPTION OF THE INVENTION

The cerebral vasculature device comprises:

Continuous braided structure comprising a plurality of wires, the braided structure having a proximal portion, a distal portion, a first expandable portion between the proximal portion and the distal portion, and a lumen extending from the proximal portion to the distal portion;

The proximal portion and the distal portion each having an outer diameter and an inner diameter and further including polymer imbedded at least partially into the braided structure;

Core wire having a proximal end and a distal end, the core wire located within the lumen and extending from the braided structure proximal portion to a point at or distal to the braided structure distal portion; and Atraumatic component attached to the core wire distal end and having an outer diameter at least equal to the inner diameter of the braided structure distal portion.

The invention is best understood with reference to the several figures that demonstrate certain exemplary, non-limiting, aspects of the invention.

Figure 1:
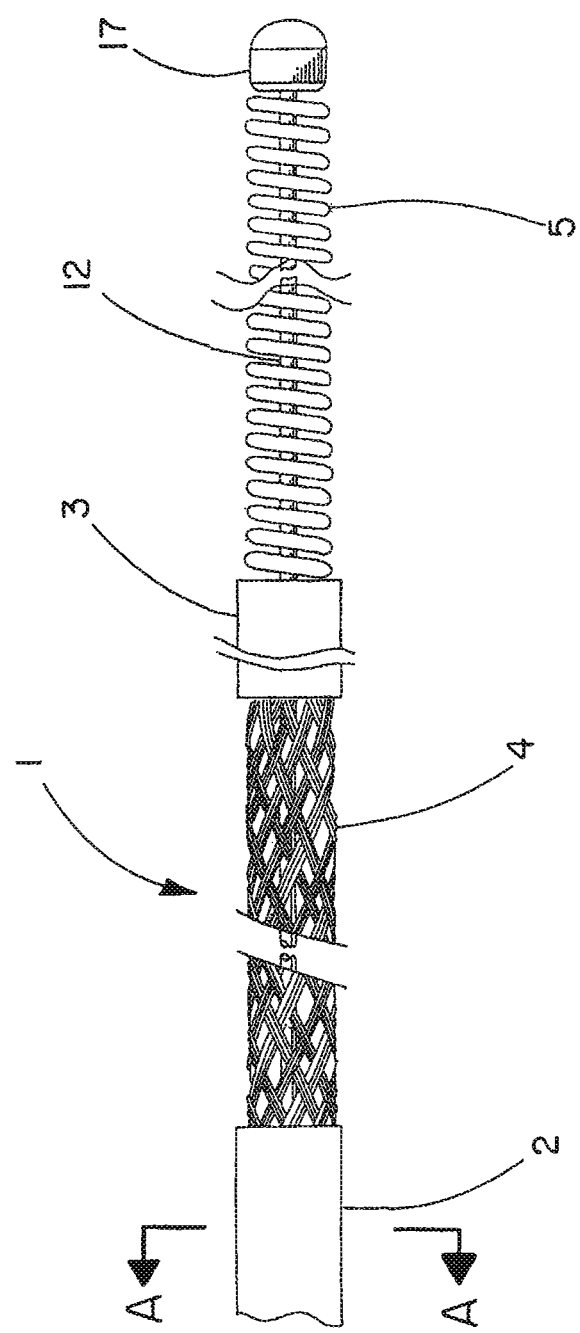
FIG. 1 shows a representative cerebral vasculature device according to an aspect of the invention.

Referring to FIG. 1, there is shown a cerebral vasculature device 1, according to the present invention. As shown, cerebral vasculature device 1 comprises a proximal portion 2, a first expandable portion 4, a distal portion 3, and atraumatic component 5. The device includes a continuous braided structure having an outer diameter, an inner diameter and a lumen that extends from the proximal portion of the continuous braided structure to the distal portion thereof. The proximal portion 2 and the distal portion 3 further include polymer 6 imbedded at least partially into the braided structure (shown in FIG. 2). The device 1 further includes core wire 12 having a proximal end and a distal end; the core wire is located within the lumen and extends from the braided structure proximal portion to a point distal to the distal most portion of the braided structure distal portion. The core wire 12 can be a ground tapered stainless steel wire, but could also be any number of materials including, but not limited to, nitinol wire, polymeric filament (including, but not limited to, expanded polytetrafluoroethylene ("ePTFE"), polyester, Kevlar® fibers), tubular structures, etc. The core wire 12 distal end extends through and is attached to atraumatic component 5, in this case a coil. Other suitable materials can be used for atraumatic component 5, such as a polymeric tubular structure. Atraumatic component 5 has an outer diameter at least equal to the inner diameter of the braided structure distal portion 3. Also shown is tip 17 at the distal tip of core wire 12 and atraumatic component 5.

Figure 2:
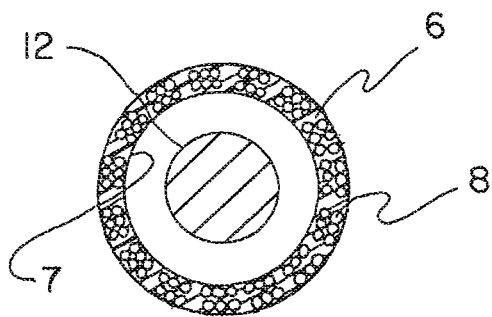
FIG. 2 shows a schematic cross-section of the device of FIG. 1.

FIG. 2 is a cross-section of the device depicted in FIG. 1 taken along A-A, wherein polymer 6 is shown imbedding braided structure 8. Moreover, lumen 7 is shown being defined by the inner diameter of the braided structure 8 and polymer 6. Also shown is core wire 12, located in lumen 7.

Figure 2A:
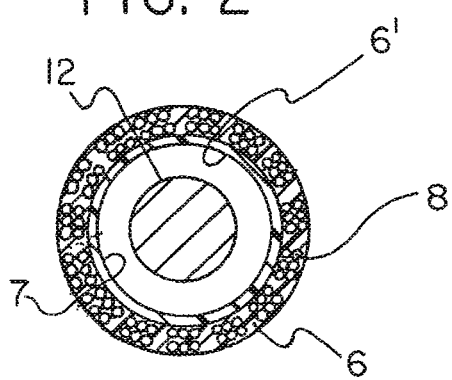
FIG. 2A shows a variation of the device of FIG. 2.

FIG. 2A shows an alternative to FIG. 2 wherein lumen 7 is defined by an inner polymer layer 6. Inner polymer layer 6 can be any suitable polymer material and can be provided as a coating, a thin tube, etc. In an aspect of the invention, inner polymer layer 6 comprises a lubricious polymer, such as polytetrafluoroethylene. In a further aspect of the invention, inner polymer layer 6 is formed by the same polymer used to imbed the braided structure. Inner polymer layer 6 can extend any desired length of the device. In an aspect of the invention inner polymer layer 6 extends from the proximal portion 2 to the distal most portion of distal portion 3.

The proximal portion 2 of the device in FIG. 1 can serve as the entire catheter shaft of the device. In a further aspect of the invention, the catheter shaft of the device may comprise a material different from the polymer imbedded braided structure. In this regard, the continuous braided structure can be part of a distal subassembly that may be attached to a suitable proximal catheter assembly.

Figure 3:
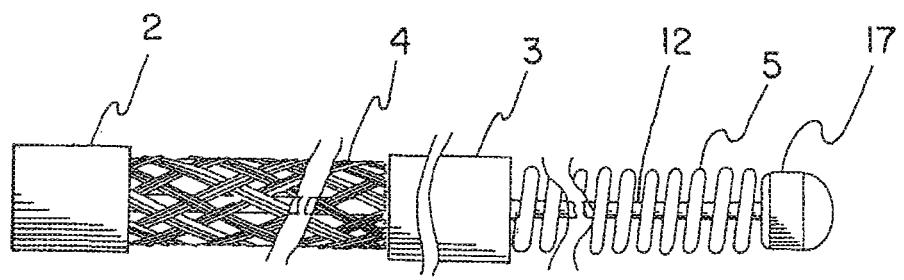
FIG. 3 shows a representative cerebral vasculature distal subassembly device according to an aspect of the invention.

Shown in FIG. 3 is a suitable distal subassembly according to an aspect of the present invention. The distal subassembly includes proximal portion 2 and distal portion 3, each comprising polymer imbedded at least partially into the braided structure. The distal subassembly further includes a first expandable portion 4 located between the proximal portion 2 and the distal portion 3. Further shown is atraumatic component 5. Also shown are core wire 12 and tip 17, located at the distal most portion of the device.

Turning now to FIG. 4A, shown is the above-described distal subassembly before being attached to catheter shaft 9. Catheter shaft 9 can comprise any suitable tubular structure, such as polymer imbedded braided structure, polymer tubing, metal tubing (such as hypo tube), etc. The tubular structure can have a change in flexibility from a proximal point to a distal point thereon. In an aspect of the invention, the distal point of the tubular structure can be more flexible than the proximal point. Catheter shaft 9 also includes a lumen which can extend over the entire length of catheter shaft 9. The lumen of catheter shaft 9 will be in communication with the lumen of the distal subassembly, once the catheter shaft 9 and distal subassembly are attached together. The catheter shaft 9 and distal subassembly can be either permanently or removably attached together. Any suitable means may be used to attach the catheter shaft 9 and distal subassembly. In an aspect of the invention, catheter shaft 9 and the distal subassembly are attached by bonding. The bond can be supplemented by, for example, crimping or shrink fitting a suitable tubular member over the bond region. For example, as shown in FIG. 4B, the bond region between shaft 9 and proximal portion 2 can be covered with a suitable metal tube, shown as 14. The metal tube 14 can be compressed into the outer surfaces of each of the shaft 9 and proximal portion 2 to provide a flush outer diameter surface of the device. The metal tube 14 can comprise any suitable metal. In an aspect of the invention, the metal tube 14 comprises radioopaque material. Also shown is polymer tube 15 located over metal tube 14 and the bond region. Polymer tube 15 can be any suitable polymer material. In an aspect of the invention, polymer tube 15 is a shrink-fit polymer tube. The polymer tube 15 can provide further reinforcement to the bond region.

In an aspect of the invention, the catheter shaft 9 is removably attached to the distal subassembly. Therefore, the distal subassembly may be used as an implantable device if desired. For example, it may be desirable to leave in the body the device in its expanded state to act as an occlusive device, to treat aneurysms, to act as a filter, to dilate a vessel, etc. In these instances, the distal subassembly can be made in the same manner previously described; however, a suitable mechanism for removably attaching the subassembly to the catheter shaft can be used. Any suitable means for removably attaching the distal subassembly to the catheter shaft can be used including, but not limited to, electrocorrosive means, mechanical means including friction fit, hook and loops, etc.

FIGS. 5A and 5B demonstrate one exemplary removable attachment embodiment wherein core wire 12 extends in a proximal direction from a point distal to the braided structure distal portion 3, through the expandable portion 4, to a point proximal to proximal portion 2. At a point proximal to the expandable portion 4, core wire 12 is in the form of a loop, or the core wire 12 can be attached to a loop-shaped wire. The loop is sized slightly larger than the inner diameter of the proximal portion 2 so that the proximal portion acts to constrain the loop, as shown in FIG. 5A. An actuation fiber 16 (or wire) is located through the loop on core wire 12. In an aspect of the invention, the fiber can be ePTFE fiber. Both ends of fiber 16 are pulled through the inner diameter of catheter shaft 9 through to the proximal end of the catheter. The expandable portion 4 can be fully actuated by pulling in a proximal direction both ends of the fiber 16, thus pulling the loop in the core wire to a location proximal of the proximal portion. This allows the loop in the core wire to spring open, thus maintaining expandable portion 4 in its expanded configuration, as shown in FIG. 5B. One end of the fiber 16 is then pulled from the proximal end of the catheter shaft allowing the distal subassembly to be freed from the catheter shaft. This mechanism is also useful in instances where more than one expandable section are present or when the porosity of the expandable section is controlled via a film covering. For example, a detachable distal subassembly of particular interest may have two expandable sections in which one section is sized/shaped to fit inside the neck of a cerebral aneurysm and the other section is sized to fit in the parent vessel, thus interrupting flow into the aneurysm.

Figure 6:
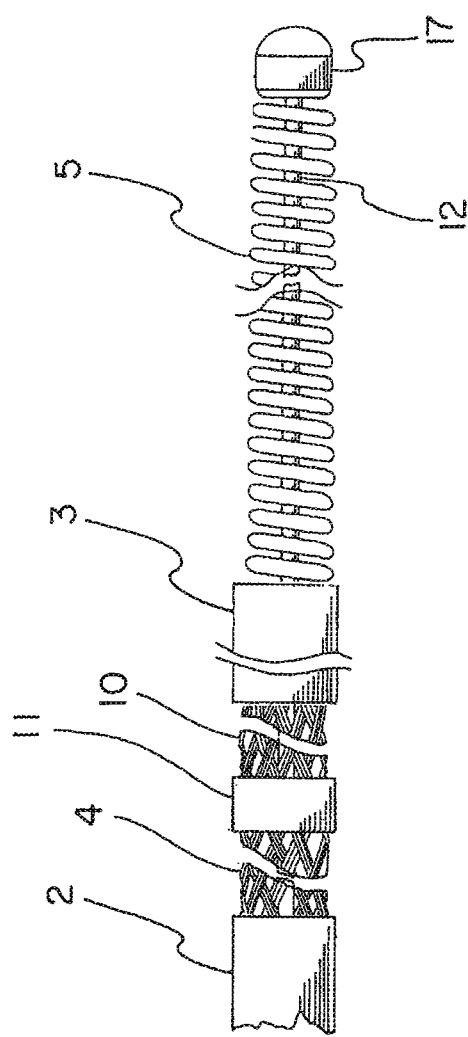
FIG. 6 shows a further representative device according to a further aspect of the invention.

FIG. 6 demonstrates a still further aspect of the present invention wherein the device includes a second expandable portion 10, located distal to the first expandable portion 4. Also shown is intermediate portion 11, which can comprise polymer imbedded at least partially into the braided structure. Intermediate portion 11 could also be formed or restrained from expansion via various other methods including, but not limited to, a change in braid angle, a marker band, a polymeric film covering, or by heat setting, etc. The intermediate portion 11 can be any suitable length. When using the device to remove thrombus from the cerebral vasculature, the first expandable portion 4 can be advanced just distal to the thrombus to be removed. Both expandable portions 4, 10 can be expanded (i.e., by moving the core wire 12 proximally), and the first expandable portion 4 can be used to pull the thrombus in a proximal direction, with the second expandable portion 10 serving as a safety feature to catch any debris that may break off from the thrombus and float in a distal direction. In an aspect of the invention, this procedure can be carried out under retrograde blood flow conditions to further limit the possibility of debris being carried in a distal direction, toward more delicate vasculature. Moreover, first expandable portion 4 and/or second expandable portion 10 can be provided with an outer polymer cover (discussed in more detail below).

In an aspect of the invention (as mentioned above) the intermediate portion 11 can comprise a braided structure having a different braid angle from the braid of the proximal section 2 and the distal section 3. For example, shown in FIG. 7A is an alternative device according to an aspect of the invention. The device includes proximal portion 2, expandable portions 4 and 10, with intermediate portion 11 located between the expandable portions 4 and 10. The device further includes core wire 12, atraumatic component 5 and tip 17. By carefully selecting the braid angle of intermediate portion 11, it is possible to restrain this section from expanding (or limit the degree of expansion relative to the expandable portions 4 and 10) without having to imbed the intermediate braid with polymer or otherwise provide a constraining means. Shown in FIG. 7B is the device with the expandable portions 4 and 10 in their expanded states. It should be understood that although the figure shows intermediate portion 11 having the same outer diameter as when the expandable portions 4 and 10 were in their unexpanded states, it is possible to adjust the braid angle of intermediate portion 11 such that the portion expands in diameter any desired amount, thus controlling the distance between the expandable portions 4 and 10 when expanded.

In a further aspect of the invention, the distance between two expandable portions can be controlled by providing a second device with a lumen or hollow core wire to allow for an appropriately sized device according to the invention to be advanced through the lumen or hollow core wire to a point distal to the second device. For example, as shown in FIG. 8, a first device comprises proximal portion 2, distal portion 3, and expandable portion 4 located therebetween. The first device further includes core wire 12, atraumatic component 5 and tip 17. The first device is shown having been at least partially advanced through the lumen of a second device. The second device comprises proximal portion 2, distal portion 3, and expandable portion 4. The second device also comprises a lumen or hollow core wire (not shown) sized to allow the first device to pass therethrough. The second device can include any suitable means to cause expandable portion 4 to expand, and preferably includes an atraumatic component, such as discussed above. In an aspect of the invention, the second device also includes a core wire (i.e., a hollow core wire), an atraumatic component attached to the core wire, and may also include a tip, as discussed above. The tip will also be hollow to allow for advancement of the first device therethrough.

Turning now to FIG. 9, there is shown a longitudinal schematic partial cross-section of a device according to an aspect of the invention. Shown in cross-section is proximal portion 2 comprising polymer 6 imbedding the braided structure 8. Also shown is first expandable portion 4 and distal portion 3 comprising polymer imbedding the braided structure. Further shown is core wire 12, extending from the proximal end of the device, through the lumen, and being attached to atraumatic component 5. Atraumatic component 5 has an outer diameter just larger than the inner diameter of distal portion 3. In an aspect of the invention core wire 12 extends from the proximal end of the device, through the lumen, and is attached to the proximal end of atraumatic component 5.

FIG. 10 shows the device of FIG. 1, where the expandable portion 4 is in its fully expanded state. Expandable portion 4 can be expanded when core wire 12 is proximally retracted while the braided structure proximal section is held fast. In an aspect of the invention, the expandable portion 4 is atraumatic to a patient's target vessel when it is in its maximum expanded state. Moreover, the maximum expanded diameter can be equal to or larger than the diameter of the patient's target vessel.

Figure 11:
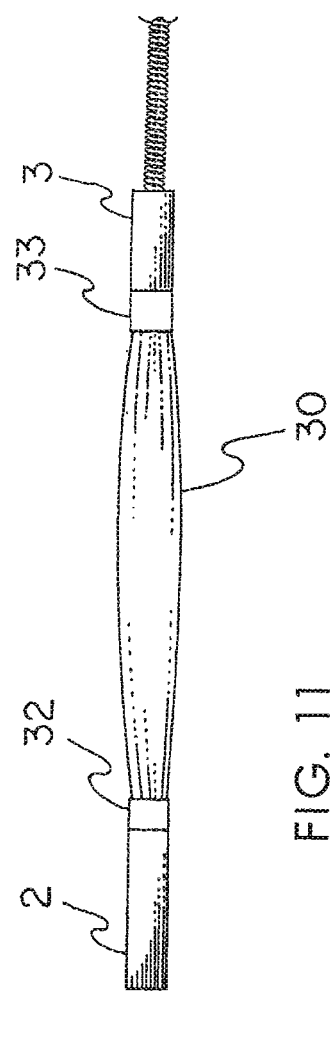
FIG. 11 shows a further embodiment of the device according to the invention.
Figure 12:
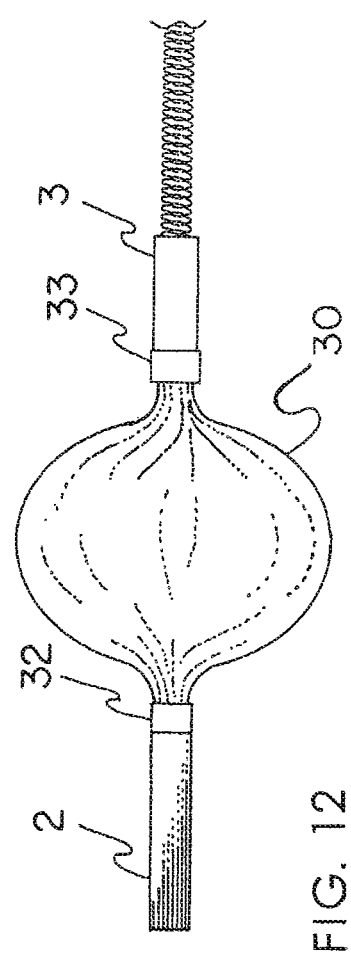
FIG. 12 shows the device of FIG. 11 wherein the first expandable portion is in its expanded state.

In a further aspect of the invention, the first expandable portion (and/or the second expandable portion) can be provided with an outer polymer cover. Shown in FIG. 11 is an example of such a device. The device is essentially the same as depicted in the figures discussed above, with the addition of the polymer cover 30 surrounding and completely covering the expandable portion. FIG. 12 shows the device of FIG. 11 wherein the expandable portion is in a partially expanded state. Any suitable polymer film, tape, etc. can be used to cover the expandable portion in a radially distensible manner. For example, suitable polymers include polytetrafluoroethylene (e.g., ePTFE), polyurethane, silicone, polyester, polyethylene, and bioabsorbable polymers. Polymer covering can be 100% occlusive in nature, or can have any variation of porosity allowing for a controlled flow rate or particle separation.

In an aspect of the invention, the polymer cover can comprise any suitable number of layers of ePTFE film which can be fused together with heat, then wrapped around expandable portion 4 in such a manner that its microstructure allows the expandable portion 4 to freely radially expand. For example, ePTFE polymer covering can comprise interconnected nodes and fibrils, with the covering arranged such that the fibrils are oriented longitudinally when the covering is in its small diameter state. Upon expansion to its larger diameter state, the fibrils can rotate and be oriented more circumferentially. Upon collapse, the ends of the covering can be pulled out as the expandable portion lengthens. This will act to realign the fibrils longitudinally. This same film can then collapse when the expandable portion is allowed to collapse underneath it. In an exemplary embodiment, 4 layers of ePTFE film can be stacked one on top of the other and wrapped around a 5 mm stainless steel mandrel in a "cigarette" wrap configuration, with the film being oriented such that the majority of fibrils are perpendicular to the axis of the mandrel. Although any suitable ePTFE film can be useful, with various wrap orientations as well, particularly attractive is an embodiment that comprises 4 layers of ePTFE film having a density of about 0.3 g/cc, a 50 micron fibril length, and a film thickness of about 0.03 mm. Once positioned on the mandrel, the film can be heated at about 370° C. for about 25 minutes to fuse together the layers of film, thus forming a tubular wall on one layer. The tube can be cut to a length of about 4 inches and removed from the mandrel. A 0.012 inch mandrel can then be positioned into the inside diameter of the tubular structure. The tubular structure can then be stretched/necked down to a point where the tubular structure's inner diameter is essentially equal to the outer diameter of the mandrel. The tubular structure can be removed and positioned over a suitable device according to the invention, with only a slight interference fit. Two Pt/Ir marker bands can then be placed over the tubular structure at points located over the proximal portion and the distal portion. A radial crimper can be used to crush the Pt/Ir bands down onto the proximal and distal portions of the device. The crimping step can be carried out under suitable heat to melt or soften the polymer portion of the proximal and distal portions, thus allowing the bands to be imbedded into the polymer to result in a flush outer surface of the device as well as to increase the strength of the bond. In an aspect of the invention, the polymer at the proximal and distal portions can comprise PEBAX® 7033 polymer and during the crimping step heat can be applied at 250° F. for about 6 seconds under 40 psi of air pressure. A steel mandrel can be placed inside the lumen of the device during the crimping step to prevent collapse of the device during heating and crimping.

The polymer cover need not be bonded to the expandable section. However, as noted above, the polymer cover should be fixedly attached to the proximal and distal portions of the device, but should be free to move over the expandable section. The polymer cover 30 can be secured to proximal portion 2 and distal portion 3 in any suitable manner. In an aspect of the invention, as shown in FIGS. 11 and 12, the polymer cover is secured to the proximal portion 2 and distal portion 3 using metal tubes 32 and 33, respectively. As mentioned above, the metal tubes 32 and 33 can be compressed into the outer surfaces of each of the proximal portion 2 and distal portion 3 to provide flush outer surfaces on each portion. The metal tubes 32 and 33 can comprise any suitable metal. In an aspect of the invention, the metal tubes comprise radioopaque metal.

By providing the first and/or second expandable portion with a polymer cover, the device may be particularly useful in disrupting flow to an aneurysm or across an arterial-venous malformation, or in preventing the distal flow of debris in the case of loose emboli. In some instances, macroporosity may be desired to allow the flow of blood through the device while filtering out debris. In an aspect of the invention, a film covering having 100 micron pores placed with a laser and an anticoagulant coating could be used to prevent the flow of debris larger than 100 microns. Devices embodying this aspect of the invention will be particularly useful due to the small profiles afforded by this invention allowing the devices to be delivered to the neurovasculature through a microcatheter.

The braided structure of the device can comprise a plurality of wires selected from, for example, the group consisting of round profiles, flat profiles, and combinations thereof. In an aspect of the invention, a majority of the wires have a round profile. In a further aspect of the invention, the majority of round wires have an outer diameter of about 0.002 inch or less. In a still further aspect of the invention, the wires have an outer diameter of 0.0015 inch or less. In a still further aspect of the invention, the majority of wires have an outer diameter of about 0.001 inch or less.

The wires can comprise any suitable material. In an aspect of the invention, the wires comprise metal. Particularly attractive wires can comprise nitinol. In a further aspect of the invention, the wires can comprise radioopaque material. In a still further aspect of the invention, the radioopaque material can comprise a metal selected from the group consisting of platinum, iridium, gold and platinum/iridium alloy.

The braided structure can comprise any number of wires. In an aspect of the invention, the braided structure comprises 32 wires or more. In a further aspect of the invention, the braided structure comprises 48 wires or more. In a still further aspect of the invention, the braided structure comprises 60 wires or more.

Figure 13:
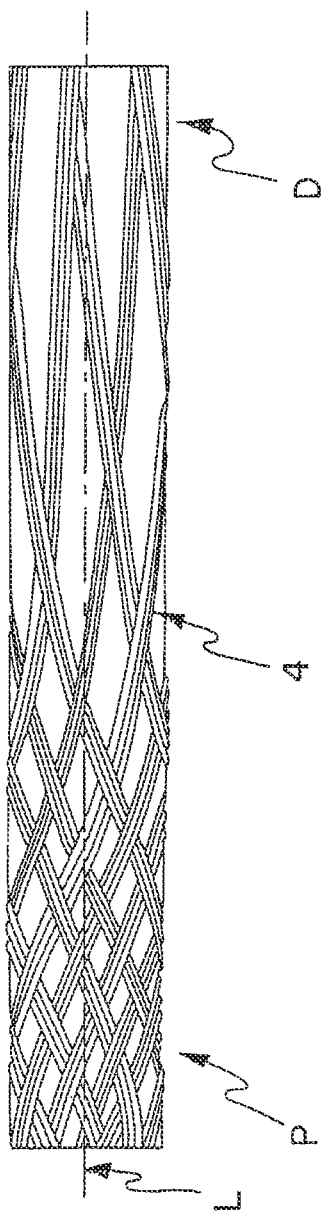
FIG. 13 shows a braided construction according to an aspect of the invention.

The braided structure can comprise wires oriented at any suitable braiding angle. In an aspect of the invention, the braided structure of the first expandable portion comprises a plurality of wires oriented at a first angle, while at least a portion of the device comprises braided structure comprising wires oriented at a second angle different from the first angle. In a further aspect of the invention, the braided structure of the first expandable portion comprises wires oriented at an angle of about less than or equal to 10 degrees, as measured from the longitudinal axis of the braided structure. In a still further aspect of the invention, the braided structure of the first expandable portion comprises wires oriented at an angle of about less than or equal to 8 degrees, as measured from the longitudinal axis. In a still further aspect of the invention, at least a portion of the proximal portion and the distal portion comprise a plurality of wires oriented at the same angle as that of the wires of the first expandable portion. In a further aspect of the invention, at least a portion of the proximal portion comprises a plurality of wires oriented at an angle different from the first expandable portion. For example, shown in FIG. 13 is braided structure 4 comprising braided wires. At the proximal end P of the braided structure, the wires are braided at a first relatively high angle, while the wires at the distal end D are braided at a second, relatively low angle, the braid angles being measured from the longitudinal axis L of the braided structure. This aspect of the invention may be particularly useful in that the higher angle braided portion may find utility as a catheter shaft that is more kink resistant than a shaft formed with a relatively lower braid angle. Moreover, the lower braid angle may be particularly useful as the expandable portion (lower braid angles may allow for proper expansion of the expandable portion when compared to higher braid angles).

It should be understood that a desired braid angle can be obtained using readily available braiding machines by setting the machine setting to a desired pics per inch (PPI) setting. The higher the PPI, the higher the braid angle. Particularly attractive devices can have an inner diameter of about 0.01 inch and may comprise an expandable portion having a braid angle of about 7 degrees (i.e., about 26 PPI), and a proximal portion having a braid angle of about 21 degrees (i.e., about 80 PPI). Thus, using well known braiding machines, braided structures according to the invention can be fabricated with any number of sections with varying braid angles. As mentioned, the braid angles are obtained by entering settings into the machine. Thus, use of such machines can result in "transition regions" being formed in the braided structure. As the machine setting changes from one setting to the next, the braid angles will be somewhere between the two set angles in this transition region.

Figure 14:
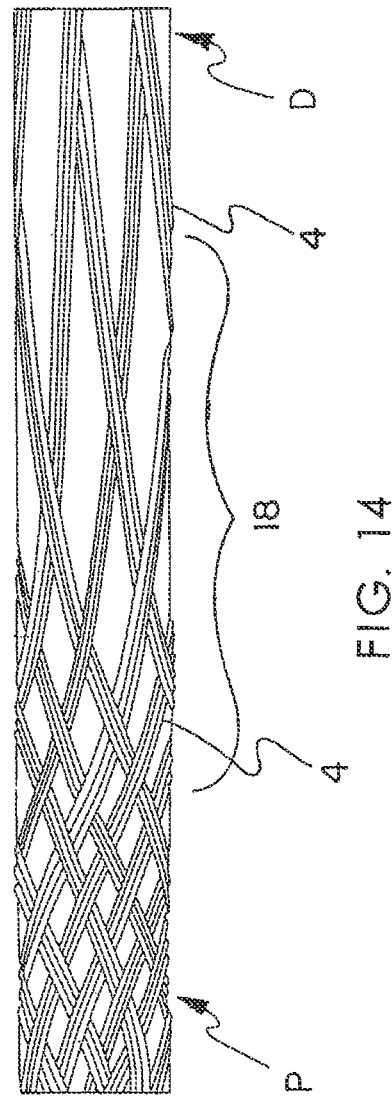
FIG. 14 shows a braided construction according to an aspect of the invention.

Such a transition region is shown, generally, as area 18 in FIG. 14. Several methods can be used to reduce the size of, eliminate, or cover over the transition region. For example, the size of the transition region can be reduced (and even eliminated) by stopping the braiding machine, changing the braid angle setting while the braided structure is held fast, and then restarting the machine. In an aspect of the invention, the braid will change from a higher angle to a lower angle in less than a centimeter. In a still further aspect of the invention, the braid will change from a higher angle to a lower angle in less than 5 mm. In a still further aspect of the invention, the braid will change from a higher angle to a lower angle in less than 3 mm.

Moreover, the transition region could be covered or partially covered with, for example, a metal or polymer tube or scrimp to add, for example, rigidity to the transition region. Furthermore, the braided structure with a transition region could first be at least partially imbedded with suitable polymer, and then a metal tube (preferably a radioopaque material) can be heated and compressed around the transition region of the braided structure to form a suitable device. If the metal tube comprises radioopaque material, the tube can serve as a marker band to help the physician guide the device to a desired target region.

Figure 15:
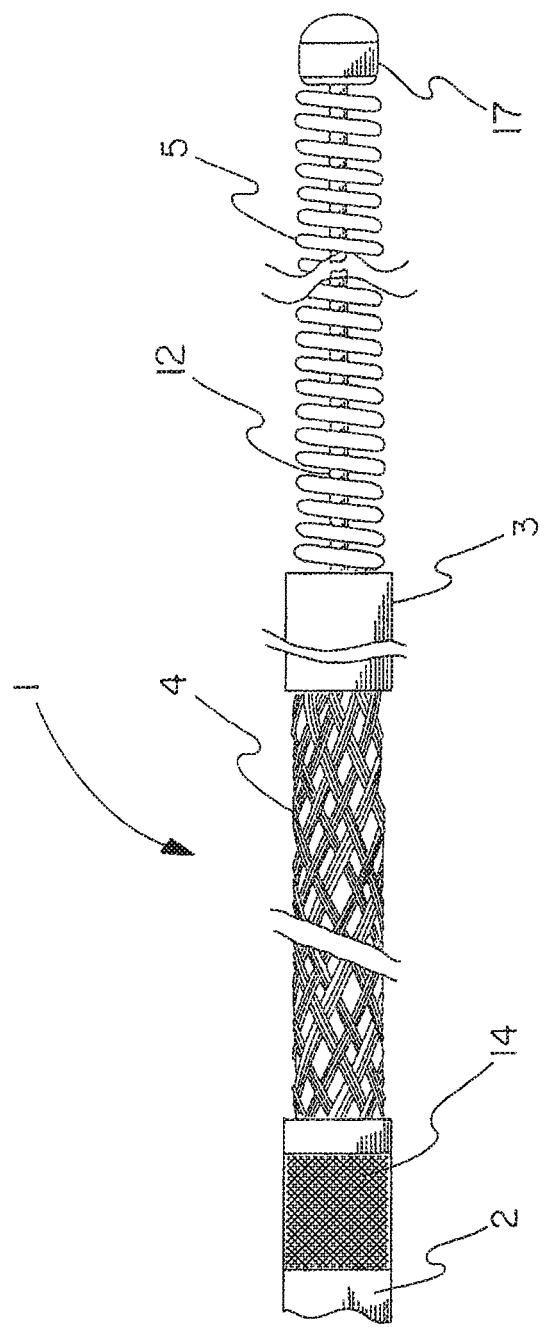
FIG. 15 shows a further representative device according to an aspect of the invention.

The above-described embodiment is shown, for example, in FIG. 15, where metal tube 14 has been located over a transition region located just proximal to expandable portion 4. As with the use of the metal tube to cover a bond region (discussed above), the metal tube 14 in this embodiment may also be imbedded into the surface of proximal portion 2 to be flush with the outer diameter of the proximal portion. Thus, providing a relatively smooth, continuous outer surface along the length of the device. Furthermore, the metal tube can comprise any suitable metal. In an aspect of the invention the metal tube comprises radioopaque material. Of course, an additional marker band can be located distal to the expandable portion 4, if desired.

In an aspect of the invention, the transition region can be eliminated by bonding together two or more sections of braided structure of differing braid angles.

The polymer imbedded at least partially into the braided structure of the proximal portion, the distal portion, and, when used, the intermediate portion, can comprise any suitable polymer material. For example, the polymer may comprise a material selected from the group consisting of polyimide, PEBA, polyurethane, nylon, polyethylene, and silicone. Moreover, the polymer can further comprise suitable filler material. For example, a suitable polymer can comprise polyimide containing PTFE filler distributed throughout the polymer. In an aspect of the invention, the polymer substantially completely imbeds the braided structure for essentially the entire length of the proximal portion, the distal portion, and, when used, the intermediate portion. Moreover, an outer polymer layer can be provided to provide the device with a polymer cap. The polymer cap will increase the outer diameter of the braided structure and can further modify the properties of the device. The polymer should be selected to provide the necessary rigidity to the device to allow the physician to advance the device and also provide structural support to the device so that when the expandable portion is expanded (e.g., by pulling proximally on the proximal end of the core wire) the remainder of the device outer diameter remains substantially unchanged. Moreover, the polymer should also provide the necessary flexibility to the device to allow the device to be advanced through the delicate cerebral vasculature. Furthermore, the composition of the polymer can be varied along the length of the device to provide for varying flexibility along the length of the device.

In a further aspect of the invention, the polymer material may comprise radioopaque material. For example, the polymer may comprise a material selected from the group consisting of barium sulfate, bismuth trioxide, etc.

In an aspect of the invention, the braided structure proximal portion and distal portion can have outer diameters of about 0.020 inch or less. In a further aspect of the invention, the braided structure proximal portion and distal portion can have outer diameters of about 0.017 inch or less.

In a further aspect of the invention, the braided structure can have an inner diameter of about 0.010 inch and an outer diameter of about 0.014 inch. Moreover, in such an embodiment, the polymer can have an inner diameter of about 0.010 inch and an outer diameter of about 0.016 inch when fully impregnating the braided structure, thus providing a 0.001 inch polymer cap around the proximal portion and the distal portion of the braided structure. In a still further aspect, at least some of the polymer can be impregnated to serve as an inner liner for the proximal portion and the distal portion. In such a case, the polymer can define an inner diameter of about 0.010 inch (with the braid having an inner diameter of about 0.011 inch) and an outer diameter of about 0.015 inch. Moreover, the braided structure can have an outer diameter of about 0.015 inch. Further, when the device proximal portion is attached to a suitable tubular structure (e.g., a catheter shaft), the tubular structure can have essentially the same inner and outer dimensions as the braided structure proximal and distal portions.

As stated, the device includes atraumatic component 5. The atraumatic component can be in the form of polymer tubular structures, metal coils, etc. When the atraumatic component comprises metal coil, the metal may comprise a material selected from the group consisting of, for example, platinum, platinum/iridium, stainless steel, and nitinol. In an aspect of the invention, the atraumatic component comprises radioopaque platinum/iridium alloy. While the atraumatic component should have an outer diameter larger than the inner diameter of the distal portion, it may also further comprise a section of reduced outer diameter that enters the lumen of the distal portion to aid in centering the core wire in the lumen of the braided structure. This section of the atraumatic component could be a coil of tapering diameter or a second coil, etc.

The device further includes a core wire that may extend essentially the entire length of the device, wherein the distal end of the core wire is attached to the atraumatic component. The core wire can comprise, for example, a material selected from the group consisting of stainless steel and nitinol or from a group of polymeric filaments including ePTFE, polyester, Kevlar® fibers, etc. or a multifiber composite. It can further comprise a tapering outer diameter, resulting in, for example, increasing flexibility of the device distally. The distal end of the core wire may contain a section which has been rolled to a rectangular profile allowing for shaping of the atraumatic tip by the physician using standard techniques. Moreover, the core wire can be a tubular structure of any suitable material, such as a polymer tube or a metal tube or a film tube comprised of discrete layers of ePTFE film which have been fused together to form a tube. The tubular structure can be solid or hollow. When the tubular structure is hollow, the hollow tube can be designed to allow for a second device, or a suitable fluid (such as contrast fluid, an oxygenated fluid, or a thrombolytic agent), to be passed through the tube to a point distal to the distal portion of the cerebral vasculature device.

Figure 16:
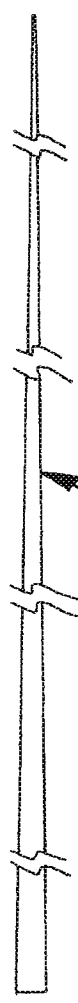
FIG. 16 shows a core wire according to an aspect of the invention.
Figure 17:
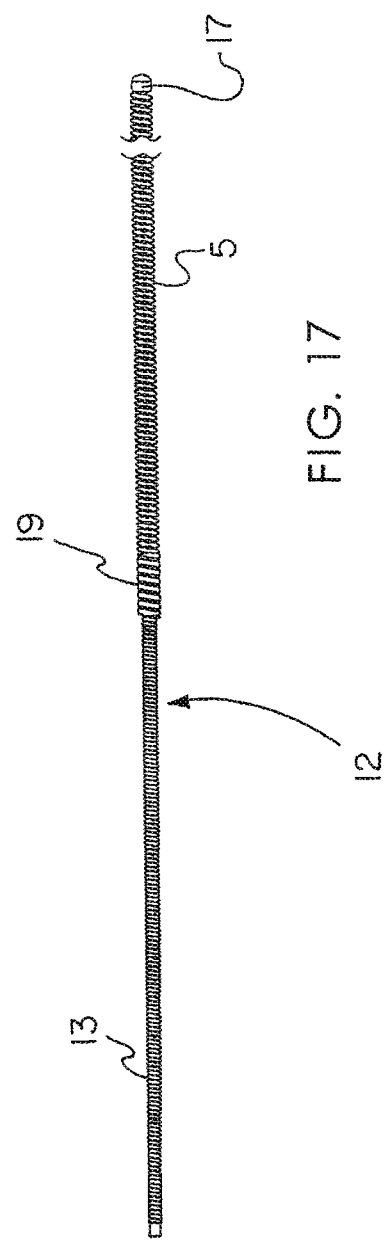
FIG. 17 shows a core wire and atraumatic component assembly according to an aspect of the invention.

Shown in FIG. 16 is a representative core wire 12. As can be seen, the core wire outer diameter is gradually tapered down from a first, relatively larger outer diameter at one end, to a second, relatively smaller outer diameter, to a third relatively even smaller diameter, etc. Any number of distinct tapered sections can be provided, or a relatively constant taper over the entire length of the wire can be provided. As shown in FIG. 17, the core wire 12 can be provided with one or more outer coils 5 and 13 fit over the core wire 12. The outer coils 5 and 13 can be used to vary the stiffness of the core wire along its length, for example. The outer coils can be, for example, metal and can be soldered (or otherwise attached, e.g., glued, etc.) to the core wire 12 at one or more points along the length of the core wire. In an aspect of the invention the coil(s) can be radioopaque metal such as, for example, platinum, gold, iridium, or platinum/iridium alloy. As shown, coils 5 and 13 overlap each other and are soldered to core wire 12 at 19. Moreover, as shown, coil 5 also includes tip 17 soldered (or otherwise attached) to the distal end of core wire 12. In an aspect of the invention, coil 5 can be located distal to the distal portion of the braided structure. Moreover, at least a portion of coil 13 can extend proximally into the distal portion of the braided structure when the device is assembled.

It should now be understood that the first expandable portion is expanded when the physician pulls the proximal end of the core wire in a proximal direction while holding the catheter shaft stationary. The atraumatic component then applies a proximal force to the distal portion of the device, which results in the first expandable portion radially expanding. The polymer imbedded into the braided structure of the proximal portion and the distal portion serves to radially constrain these portions, thus preventing them from expanding.

The device can further comprise at least one radioopaque marker band. The marker bands can be any suitable radioopaque material, such as those described above. In an aspect of the invention, the at least one radioopaque marker band can lie in a recess provided in the polymer material. The at least one radioopaque marker band can be provided proximal and/or distal to the first expandable portion.

In an aspect of the invention, the expandable portion has a length in its unexpanded state of about 1 cm or less. In a further aspect of the invention, the expandable portion has a length of about 5 mm or less. In a still further aspect of the invention, the expandable portion has a length of about 4 mm.

As mentioned above, the expandable portion will radially expand when the core wire is moved in a proximal direction relative to the proximal portion of the device. When expanded, the first expandable portion can have any suitable diameter. In an aspect of the invention, the maximum expanded diameter of the first expandable portion is about 6 mm or less. In a further aspect of the invention, the maximum diameter of the first expandable portion is about 4 mm or less. In a still further aspect of the invention, the maximum diameter of the first expandable portion is about 3.3 mm.

Figure 18:
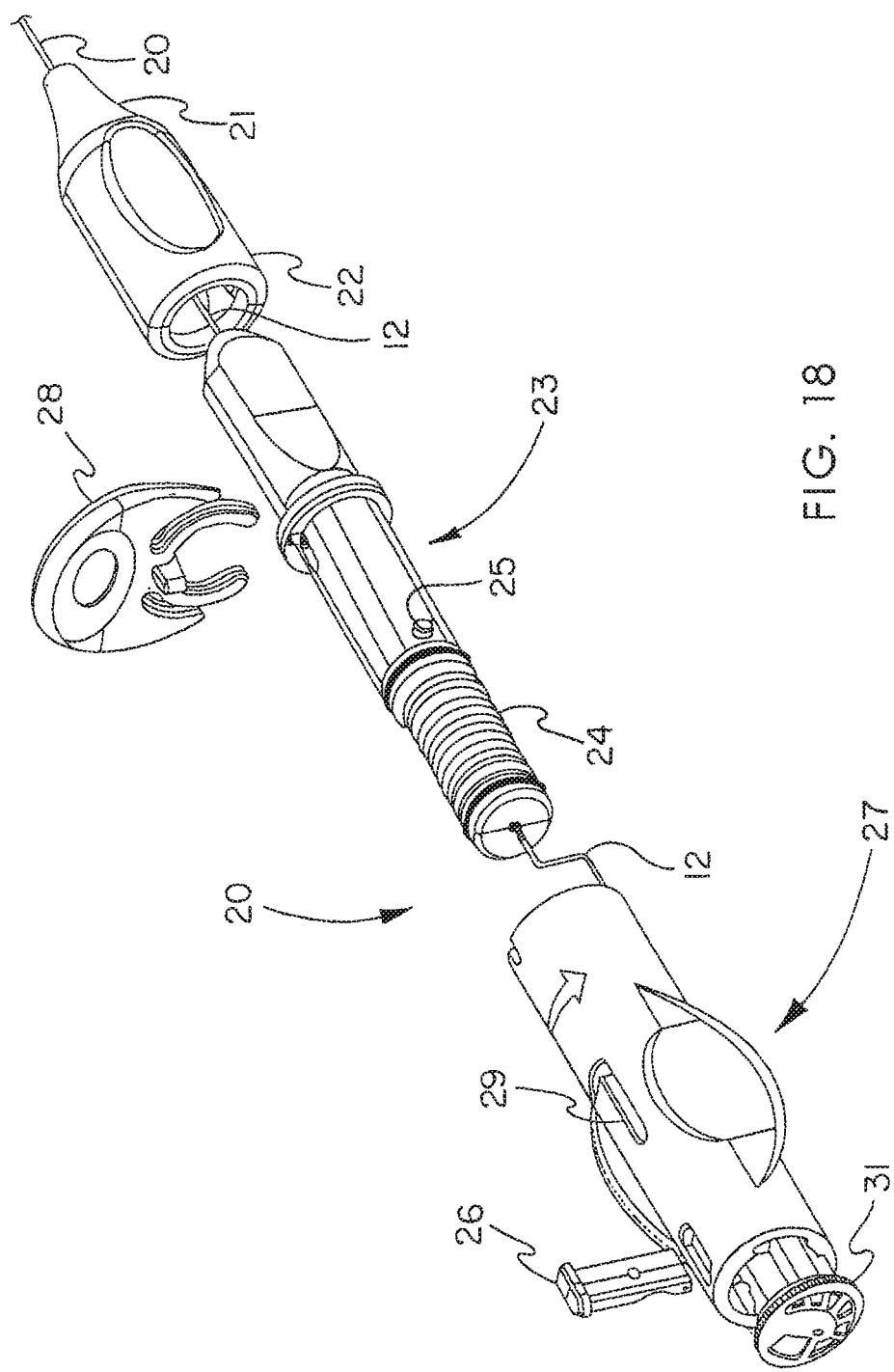
FIG. 18 shows an exploded view of a handle assembly according to an aspect of the invention.
Figure 19:
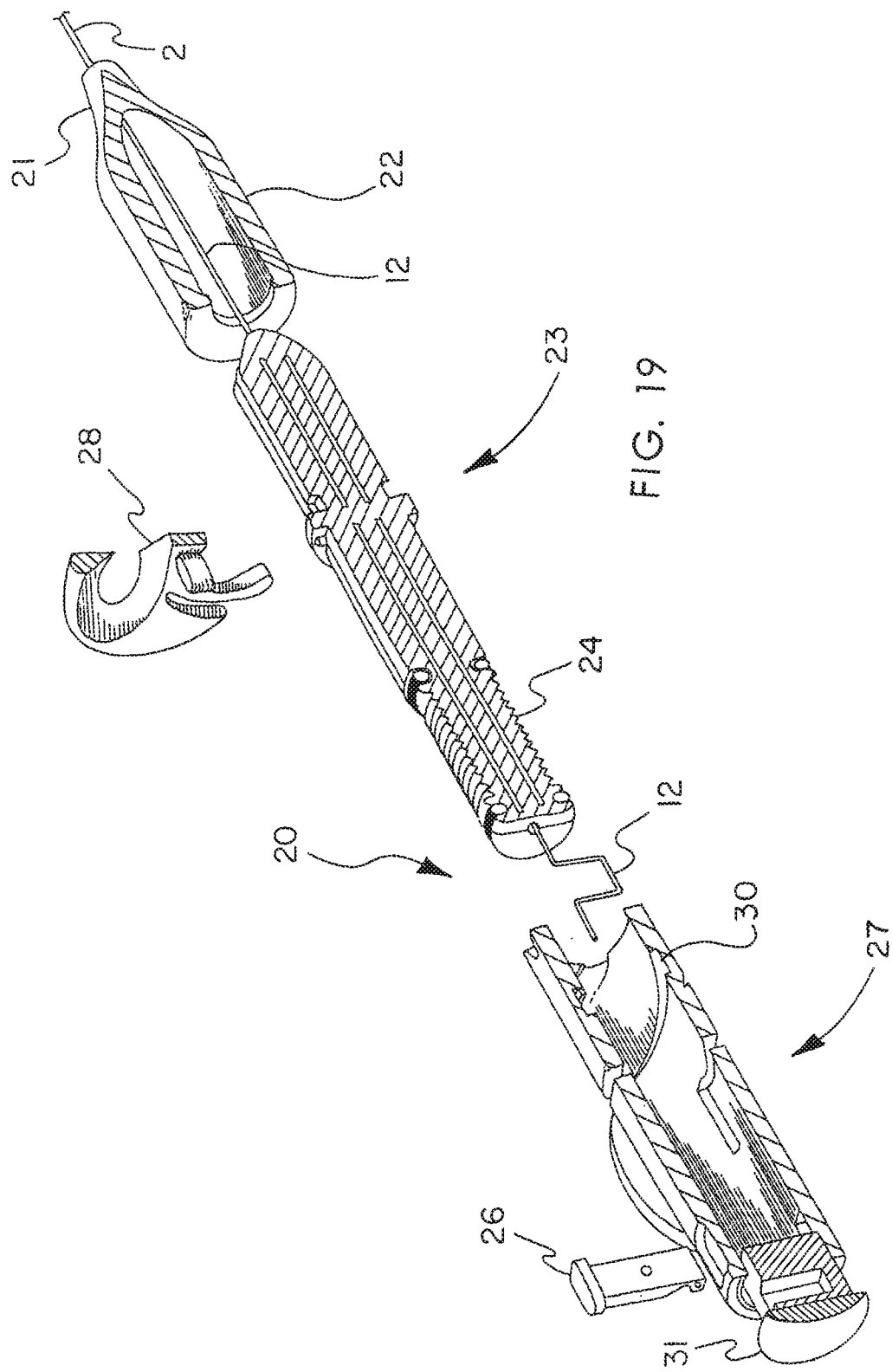
FIG. 19 shows a cross-sectional exploded view of the handle assembly shown in FIG. 18.
Figure 20:
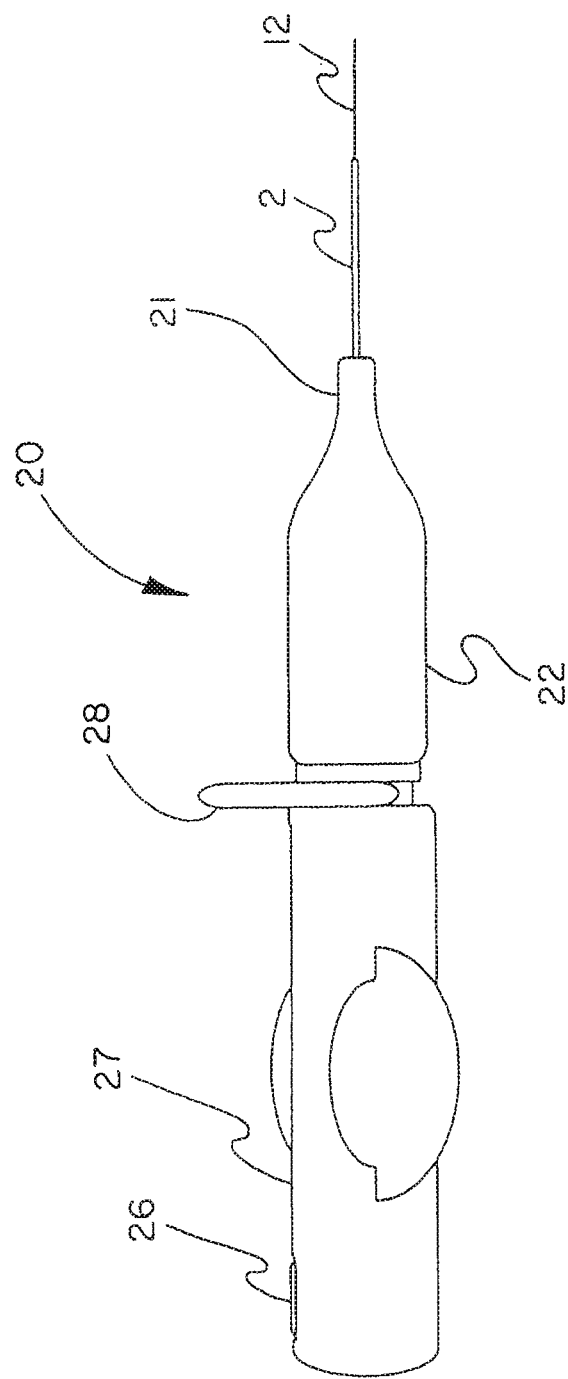
FIG. 20 shows the handle assembly of FIG. 18, fully assembled.

The device can further include a handle coupled or otherwise attached to the proximal end of the braided structure, or the proximal end of the catheter shaft as the case may be. The handle can, in addition to allowing for manipulation of the device through a patient's vasculature, be provided with a mechanism for expanding the expandable portion of the device. For example, shown in FIGS. 18, 19, and 20 is a suitable handle construction. Shown attached to the distal end of the handle 20 is the device shaft or the braided structure proximal portion 2. The handle 20 comprises a strain relief section 21 at the distal end of distal housing 22. Coupled to distal housing 22 is proximal handle portion 23 which includes ribbed section 24. Pin 26 may be provided to fix core wire 12 to the proximal housing 27. Proximal housing 27 fits over proximal portion 23. Proximal housing 27 includes cantilever arm 29. Moreover, proximal portion 23 also includes pin or protrusion 25 which is sized to fit into helical slot 30 in proximal housing 27. Finally, handle 20 can include safety lock/pin 28 and end cap 31, which is insertable into proximal housing 27.

To operate the handle 20, safety lock/pin 28 is removed and proximal housing 27 is rotated relative to proximal portion 23 and distal housing 22. Rotation will slowly withdraw core wire 12 and thus cause first expandable portion 4 (and when present, second expandable portion 10) to radially expand. The ribbed section 24, along with the cantilever arm 29 allows for incremental locking of the core wire as it is retracted.

A method for producing the device according to the present invention includes, forming the desired braided structure having a lumen extending for the length thereof. The braided structure can then be at least partially (and preferably essentially completely) imbedded with a suitable polymer material, for example, by dip coating the braided structure into a suitable polymer. Once the polymer is cured, the first expandable portion can be obtained by removing the polymer from a desired length of the braided structure near the distal tip of the structure. Suitable methods for removing the polymer include, for example, by laser ablation, abrasion (e.g., micro abrasion methods), etc.

After removing the polymer to form the first expandable portion, a suitable atraumatic component can be located at the distal tip of the device (i.e., distal to the distal end of the device). The atraumatic component need not be bonded or attached to the distal portion of the device. Suitable core wire can then be attached at its distal end to the proximal end of atraumatic component 5 and then inserted through the lumen of the distal section of the device and advanced proximally until the proximal end of the core wire extends through the lumen of the proximal section of the device.

The core wire can be any suitable material, such as any suitable metal. The core wire can be tailored to have a varying stiffness over its length (i.e., relatively stiff at its proximal end to relatively flexible at its distal end). The core wire may be attached to atraumatic component in any suitable fashion.

Without intending to limit the scope of the present invention, the following example illustrates how a device according to the present invention may be made and used.

Nitinol wire can be obtained with a nominal diameter of 0.001 inch from, for example, Fort Wayne Metals (Fort Wayne, Ind.). This wire can be wound on 16 bobbins, where 3 ends of wire are on each bobbin. This wire can be braided onto a suitable 0.010 inch mandrel (e.g., silver-plated copper) at 26 PPI (or about 7 degrees as measured from the longitudinal axis). The wire can then be dip coated with a PEBAX® 7033 resin so that the resin fully impregnates the braided structure down to the mandrel surface. Multiple dipping/heating steps can be applied until an outer diameter of 0.016 inch is obtained. This tubing can then be cut to 180 cm in length. An excimer laser of suitable wavelength can then be used to fully ablate away the polymer while leaving the wires relatively free from damage in a 4 mm section of tubing located 2 mm from the distal end of the tubing. One suitable alternative to laser ablation for removing the polymer to form the expandable portion includes removing the polymer by abrasion utilizing a suitable abrasive material in a high velocity gas stream. In one exemplary method, sodium bicarbonate with an average particle size of 25 microns can be mixed into an airstream at 30-120 psi and directed to a portion of the tubing through a small orifice. Upon impingement of the surface, the abrasive particles will act to remove the polymer at little or no detriment to the wires. A core wire consisting of a 2 meter long stainless steel wire of 0.008 inch diameter can be obtained (for example from Precision Wire Components, PWC, Tualatin, Oreg.). The wire can be ground down over its distal 25 cm with a taper to 0.002 inch in diameter. The distal 1 cm can be rolled flat with a short edge of 0.001 inch. A small coil of 0.0015 inch platinum/iridium alloy wire can be manufactured with a tapering outer diameter of 0.010 inch to 0.007 inch and a length of 11 mm. This coil can be soldered onto the core wire 28 mm from its distal edge. Another coil of 0.002 inch platinum/iridium alloy wire can be manufactured to be 33 mm in length with an inner diameter of 0.010 inch. This coil can be positioned over the core wire aligned with the distal tip of the core wire and overlapping the tapered coil by about 5 mm. This can be soldered onto the smaller coil and also to the distal tip of the core wire.

The proximal end of the core wire can be assembled through the inner diameter of the braided tubing until the tapered coil is pulled into the distal portion of the device, thus centering the core wire in the lumen.

The device can be used to remove thrombus from very delicate, tortuous cerebral vasculature. One method of using the device includes introducing the device using well known techniques (for example, percutaneously introducing the device). The device can be advanced to a target region in the cerebral vasculature through the lumen of known microcatheters. Of course, use of a microcatheter may not be needed if the device is designed to have the necessary flexibility and pushability to be advanced without a microcatheter. In an aspect of the invention the device is advanced to the target region while retrograde blood flow is maintained in the target vessel. In a further aspect of the invention, the device can be advanced to a point just proximal to the target region under antegrade blood flow conditions, and under retrograde blood flow conditions as the distal tip of the device crosses the thrombus located in the target region. Retrograde blood flow can be obtained by any suitable technique, such as by applying suction to the target vessel, or by natural physiological manipulation using the methods and apparatus taught by, for example, Dorros et al. in U.S. Pat. No. 6,929,634, the subject matter of which is herein incorporated by reference. Once the thrombus is crossed by at least the first expandable portion of the device, the expandable portion can be expanded and the thrombus pulled back in a proximal direction, preferably still under retrograde blood flow conditions, to remove the thrombus from the patient. In some instances of well adhered or large thrombus, it may be particularly useful to use the expandable portion of the device to macerate or break apart the thrombus into smaller pieces by cycling the expansion and collapse of the expandable portion of the device.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A cerebral vascular device for capture and removal of thrombus, said cerebral vascular device comprising:
   a catheter defining a lumen extending longitudinally therethrough, the catheter having a continuous braided structure comprising a plurality of wires, the catheter having a proximal portion wherein a polymer is embedded substantially throughout the braided structure, the catheter having a distal portion, the catheter having first and second expandable portions disposed between the proximal portion and the distal portion and an intermediate portion located between the first expandable portion and the second expandable portion, the braided structure along the distal portion and first and second expandable portions of the catheter being exposed and not covered by the polymer, an elongated core wire extending longitudinally through the lumen; and an atraumatic component being attached to the core wire and being entirely distal of the braided structure;

wherein, in response to axial displacement of the proximal and distal portions of the braided structure toward each other, the first and second expandable portions expand radially outwardly to a maximum expanded diameter and flatten axially and the intermediate portion and remaining portions of the braided structure are restrained from axially expanding and remain aligned with the lumen of the catheter, and wherein the braid angle of the first and second expandable portions is about less than or equal to 10 degrees as measured from a longitudinal axis of the braided structure, and the intermediate portion and portions of the braided structure adjacent the first and second expandable portions have a braid angle that is substantially greater than 10 degrees as measured from a longitudinal axis of the braided structure such that the intermediate portion and remaining portions of the braided structure are restrained from axially expanding and remain aligned with the lumen of the catheter.

2. The cerebral vascular device of claim 1, wherein the braid angle of the first expandable portion is about less than or equal to 8 degrees as measured from the longitudinal axis of the braided structure.

3. The device of claim 1, wherein the plurality of wires comprise metal wires.

4. The device of claim 3, wherein the wires of the braided structure have an outer diameter of about 0.020 inch or less.

5. The device of claim 4, wherein the wires of the braided structure have an outer diameter of about 0.017 inch or less.

6. The device of claim 5, wherein the plurality of wires comprise nitinol.

7. The device of claim 4, wherein the wires have a round profile.

8. The device of claim 1, wherein the polymer comprises a material selected from the group consisting of polyimide, peba, polyurethane, nylon, silicone, and polyethylene.

9. The cerebral vascular device of claim 1, wherein the braid angle of the second expandable portion is about less than or equal to 8 degrees as measured from the longitudinal axis of the braided structure.

10. The device of claim 1, wherein the intermediate portion comprises polymer imbedded at least partially into the braided structure.

11. The device of claim 1, wherein the intermediate portion is radially constrained by a polymer covering.

12. The device of claim 1, wherein the intermediate portion is radially constrained by a metal band.

13. The device of claim 1, wherein the atraumatic component has an outer diameter at least equal to the inner diameter of the braided structure distal portion.

14. The cerebral vascular device of claim 13, wherein the atraumatic component is selected from the group consisting of polymer tubular structures and metal coils.

15. The cerebral vascular device of claim 14, wherein the metal coil comprises radioopaque material.

16. The cerebral vascular device of claim 14, wherein the radioopaque material comprises a material selected from the group consisting of platinum, gold, iridium, and platinum/iridium alloy.

17. A cerebral vascular device for capture and removal of thrombus, the cerebral vascular device comprising:

a catheter defining a lumen extending longitudinally therethrough, the catheter having a continuous braided structure comprising a plurality of wires, the catheter having a proximal portion wherein a polymer is embedded substantially throughout the braided structure, the catheter having a distal portion, the catheter having first and second expandable portions disposed between the proximal portion and the distal portion and an intermediate portion disposed between the first and second expandable portions, the braided structure along the distal portion and first and second expandable portions of the catheter being exposed and not covered by the polymer;

an elongated core wire extending longitudinally through the lumen; and an atraumatic component being attached to the core wire and being entirely distal of the braided structure;

wherein, in response to axial displacement of the proximal and distal portions of the braided structure toward each other, the first and second expandable portions expand radially outwardly to a maximum expanded diameter and flatten axially and the intermediate portion and remaining portions of the braided structure are substantially prevented from axially expanding and remain aligned with the lumen of the catheter, wherein the braid angle of the intermediate portion is configured to restrained the intermediate portion from axially expanding and to remain aligned with the lumen of the catheter.

* * * * *